United States Patent [19]
Anderson et al.

[11] Patent Number: 5,830,719
[45] Date of Patent: Nov. 3, 1998

[54] PROCESS FOR CONTINUOUSLY SPLITTING A GLYCERIDE INTO CARBOXYLIC ACIDS AND GLYCERIN

[75] Inventors: Kevin W. Anderson, Indian Springs; J. Douglas Wenzel, Cincinnati, both of Ohio

[73] Assignee: Henkel Corporation, Plymouth Meeting, Pa.

[21] Appl. No.: 843,968

[22] Filed: Apr. 17, 1997

Related U.S. Application Data

[63] Continuation of Ser. No. 456,209, May 31, 1995, abandoned.

[51] Int. Cl.$^6$ ............................... C12P 7/64; C12P 7/40; C12P 7/20; C12N 9/20
[52] U.S. Cl. ........................ 435/134; 435/136; 435/159; 435/198
[58] Field of Search ................................. 435/135, 144, 435/198, 134, 136, 159

[56] References Cited

U.S. PATENT DOCUMENTS

| | | | |
|---|---|---|---|
| 2,486,630 | 3/1949 | Brown | 260/415 |
| 4,275,011 | 6/1981 | Tanaka et al. | 260/410.7 |
| 4,275,081 | 6/1981 | Coleman et al. | 426/33 |
| 4,678,580 | 7/1987 | Brady et al. | 210/490 |
| 5,106,736 | 4/1992 | Patel et al. | 435/106 |
| 5,273,898 | 12/1993 | Ishii | 435/198 |
| 5,470,741 | 11/1995 | Oester et al. | 435/254.1 |

FOREIGN PATENT DOCUMENTS

| | | |
|---|---|---|
| 0093602 | 4/1983 | European Pat. Off. . |
| 0191217 | 8/1985 | European Pat. Off. . |
| 0188725 | 10/1985 | European Pat. Off. . |
| 2705608 | 8/1977 | Germany . |
| 3108927 | 3/1981 | Germany . |
| 61-181390 | 7/1986 | Japan . |
| 62-228289 | 10/1987 | Japan . |
| WO82/03873 | 11/1982 | WIPO . |
| WO83/0016 | 1/1983 | WIPO . |

OTHER PUBLICATIONS

Okumura, et al, "The Effect of Reverse Action on Triglyceride Hydrolysis by Lipase", *Agric. Biol. Chem.*, 45(1), 1981, pp. 185–189.

Lobyreva, et al, Institute of Microbiology, Academy of Sciences of the USSR, *Mikrobiologiya*, vol. 48, No. 1, 1979, pp. 53–56.

"Enzymatic Hydrolysis of Fats", *Henkel–Referate 23/Int. Ed.*, 1987, pp,. 29–35.

Okumura, et al, "Purification and Properties of Partial Glyceride Hydrolase of *Penicillium cyclopium* M1", *J. Biochem.*, 87, 1980, pp. 205–211.

"Synthesis of Various Kinds of Esters by Four Microbial Lipases", *Biochimica et Biophysica Acta*, 575, 1979, pp. 156–165.

"Hydrolysis of Triglyceride by Solid Phase Lipolytic Enzymes of *Rhizopus arrhizus* in Continuous Reactor Systems", *Biotechnology and Bioengineering*, vol. XXIII, 1981, pp. 1703–1719.

"Combined Enzymatic/Non–Enzymatic Fat Splitting", *Research Disclosure*, vol. 310, #336102, Apr., 1992.

*Primary Examiner*—David M. Naff
*Assistant Examiner*—Deborah Ware
*Attorney, Agent, or Firm*—Wayne C. Jaeschke; John E. Drach; Steven J. Trzaska

[57] ABSTRACT

Carboxylic acids and glycerine are made by a continuous splitting process which involves the formation of a presplitting mixture by separately adding the glyceride, an effective lipase in an amount sufficient to produce partial splitting of the glyceride, and water. The water used in the formation of the presplitting mixture is water that has been separated from the glycerin-water effluent stream from the pressure splitter and recycled. The next step involves the pressure splitting which entails mixing the partially split glyceride from the presplitter with water and heating under conditions of temperature and pressure effective to substantially complete the splitting of the glyceride into component fatty acids and a glycerin-water stream. The water is then separated from the glycerine-water stream and the water is recycled to the presplitter.

11 Claims, 2 Drawing Sheets

PROCESS FOR CONTINUOUSLY SPLITTING A GLYCERIDE INTO CARBOXYLIC ACIDS AND GLYCERIN

This application is a continuation of application Ser. No. 08/456,209 filed on May 31, 1995, now abandoned.

FIELD OF THE INVENTION

This invention relates to improvements in the pressure splitting of fats and oils by means of a presplitting step utilizing lipase hydrolysis wherein the glycerine evaporator condensate from the pressure splitter is recycled to the presplitter.

BACKGROUND OF THE INVENTION

Fats and oils are also know as triglycerides, which are the reaction products of glycerine and fatty acids. Fatty acids and glycerine can be produced by reversing the reaction between glycerine and fatty acids which is known as hydrolysis. Commercially, the hydrolysis reaction is known as "splitting" in that glycerine and fatty acids are hydrolyzed or "split" apart to break the bonds between the acid and the glycerine.

Typically, the fat or oil is split commercially in a pressure splitter wherein preferably the fat or oil is introduced at one end and water introduced at the opposite end thereof in a countercurrent flow pattern. In operation, the pressure splitter provides substantial amounts of heat and pressure to the mixture of triglyceride and water to effect the hydrolysis. However, because the triglyceride is hydrophobic, the amount of actual contact between the water phase and the fat phase is relatively low. It is believed that after a period of time in the splitter individual triglyceride molecules incompletely hydrolyze, splitting off one acid molecule to create a di-glyceride or two acid molecules to form a monoglyceride. The mono- and di-glycerides are less hydrophobic than the starting triglyceride, and mix more thoroughly with water. As a result, the mono- and di-glycerides function as emulsifiers to improve mixing of the triglyceride with water. Under the turbulent conditions within the pressure splitter, it is believed that the mono- and di-glycerides improve the extent of mixing between the triglyceride and water, thereby facilitating the hydrolysis reaction.

The period of time during which the hydrolysis rate is depressed is known as the induction period. During the induction period, heat is input to the pressure splitter and pressure is generated, but few hydrolysis products are being produced. The volume of triglycerides hydrolyzed within the pressure splitter would be increased substantially if the induction period could be eliminated or at least substantially reduced.

One way of eliminating the induction period is to employ a partial or presplitting step wherein a lipase with a minor amount of water is combined with the fat or oil feedstock with agitation prior to pressure splitting. The partial splitting step is performed during that time while the fat or oil is stored in a holding tank prior to pressure splitting. The fat or oil is typically held in a heated tank for at least two days prior to pressure splitting, and partial hydrolysis can be performed within that period of time with the aid of a lipase catalyst. The lipase is added to the presplitter as an aqueous solution. Prior to the present invention, the lipase solution was made by mixing the lipase with fresh water. The lipase solution is agitated at a rate sufficient to render the solution miscible or finely dispersed in the feedstock. The agitation is continued for a period of time sufficient to raise the acid value, and at a temperature optimally just below the deactivation temperature of the lipase. It has been found that agitation of a tallow feedstock with lipase and water for about 24 to 48 hours at temperatures of up to about 60° C. can produce acid values in the range of about 40 to about 80 (mg KOH/g sample). In comparison, complete hydrolysis of tallow would produce an acid value from the liberated carboxylic acids of about 205.

The preferred commercial presplitting process is carried out in a continuous manner as described in copending application Ser. No. 08/356,047, filed on Dec. 14, 1994, the entire contents of which are incorporated herein by reference. In the continuous process, a triglyceride to be treated, such as tallow, is introduced continuously into a reaction vessel at an elevated temperature, e.g. at about 50°–60° C. A lipase slurry in water containing from about 0.01% to about 2%, preferably about 0.08% to about 1.2% by weight of lipase is simultaneously introduced on a continuous basis into the reaction vessel. The flow rates of the triglyceride and of the tallow slurry are adjusted to provide from about 2% to about 5% by weight of water based on the weight of triglyceride, and to provide a residence time for the triglyceride in the reaction vessel of from about 24 to about 96 hours, depending on the temperature and on the activity of the lipase used in the process. Under these conditions, a steady state acid value in the effluent ranging from about 25 to about 100 is obtained, and usually from about 50 to about 100. The mixture in the reaction vessel is thoroughly mixed throughout the process, using any agitation or stirring means that will accomplish such thorough mixing. The effluent presplit triglyceride is then fed directly to a pressure splitter to complete the reaction and produce fatty acids and glycerine. Typically, the fat or oil is split commercially in a pressure splitter wherein preferably the fat or oil is introduced at one end and water introduced at the opposite end thereof in a countercurrent flow pattern. In operation, the pressure splitter provides substantial amounts of heat and pressure to the mixture of triglyceride and water to effect the hydrolysis. Fatty acids produced in the presplitter are removed by phase separation. The liquid effluent from the pressure splitter, also known as sweetwater, is sent to a disk centrifuge and then into a series of steam evaporators wherein the water is separated from the glycerine by evaporation and the evaporated water is condensed to form the glycerine evaporator condensate. It has been found that the use of fresh water in the presplitter causes problems downstream. Because of the presence of calcium and magnesium salts in the fresh water, fatty acid soaps are formed in the presplitter. The fatty acid component of these soaps is supplied by the recycled glycerine evaporator condensate. These soaps build up in the disk centrifuge and the glycerine evaporator condensate bottoms.

One solution to the downstream problems mentioned above is to use the glycerine evaporator condensate as the aqueous phase in the presplitter because of the presence of only minute amounts of calcium and/or magnesium, if any. However, it has been found mixing the glycerine evaporator condensate, the lipase, and make up fresh water inactivated the lipase in the presplitter probably due to the low pH of the glycerine evaporator condensate and the high temperature (160° F.).

SUMMARY OF THE INVENTION

The present invention utilizes the glycerine evaporator condensate from the pressure splitter as the water phase of the presplitter without the concomitant inactivation of the enzyme. The surprising discovery has been made that if the glycerine evaporator condensate from the pressure splitter is added to the presplitter separately from a lipase-fresh water slurry, the lipase does not undergo inactivation. Thus, the process according to the invention utilizes the glycerine evaporator condensate thereby minimizing the effluent emissions from a pressure splitting operation.

The present invention relates to a continuous process for the production of carboxylic acids and glycerine from a glyceride. The first step of the process involves the formation of a presplitting mixture by separately adding the glyceride, an effective lipase in an amount sufficient to produce partial splitting of the glyceride, and water. The water used in the formation of the presplitting mixture is water that has been separated from the glycerin-water effluent stream from the pressure splitter and recycled. The next step involves the pressure splitting which entails mixing the partially split glyceride from the presplitter with water and heating under conditions of temperature and pressure effective to substantially complete the splitting of the glyceride into component fatty acids and a glycerin-water stream. The water is then separated from the glycerine-water stream and the water is recycled to the presplitter.

DETAILED DESCRIPTION OF THE INVENTION

Other than in the claims and in the operating examples, or where otherwise indicated, all numbers expressing quantities of ingredients or reaction conditions used herein are to be understood as modified in all instances by the term "about".

Figure 1:
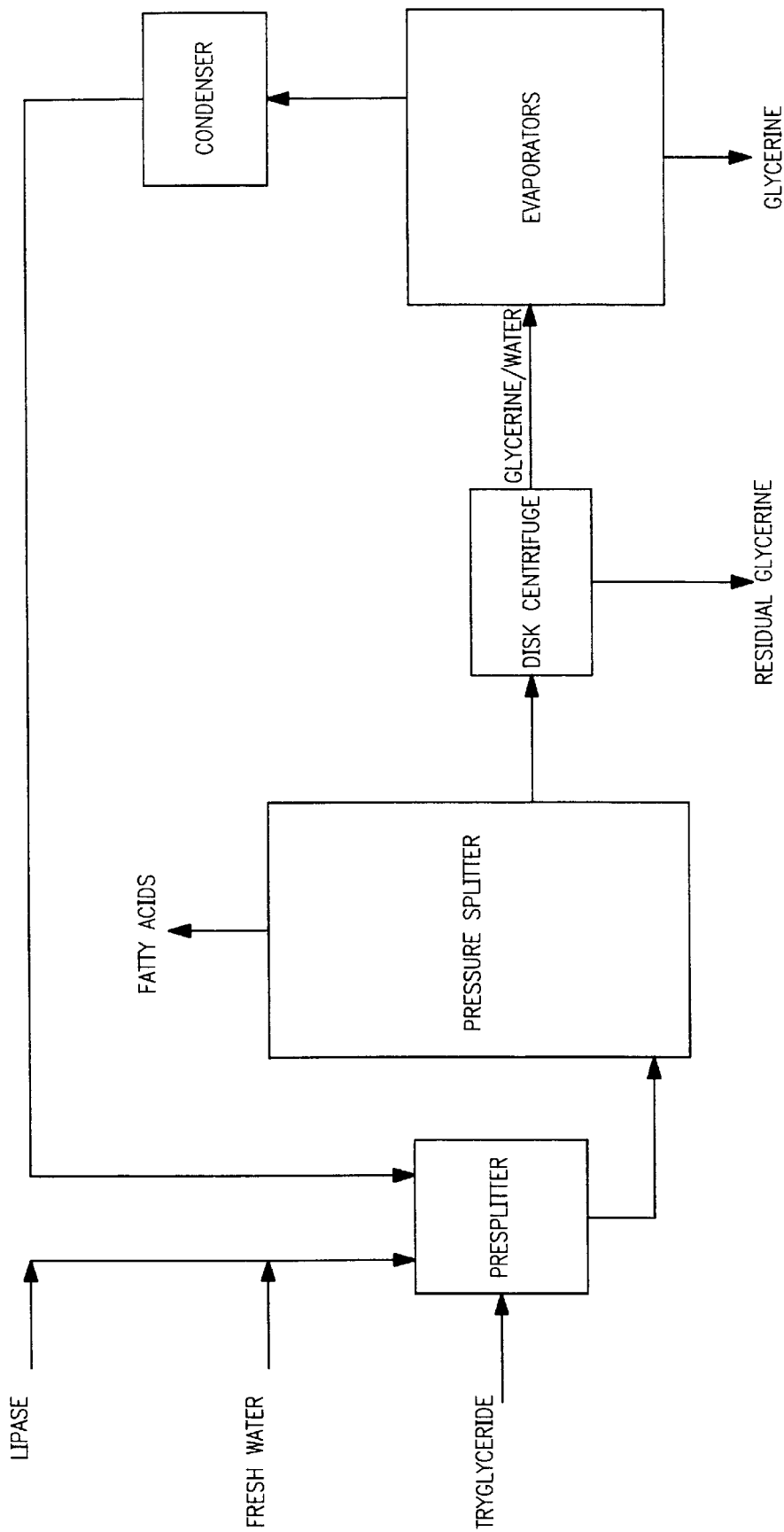
FIG. 1 is a flow chart of a fat pressure splitting process containing a presplitting operation wherein the glycerine evaporator condensate from the pressure splitter is recycled to the presplitter.

The present invention relates to an improvement in a fat pressure splitting process having a presplitting step wherein the glycerine evaporator condensate from the pressure splitter is recycled to the presplitter. The process according to the invention is depicted in FIG. 1. The triglyceride, such as tallow, is introduced continuously into the presplitter at an elevated temperature, e.g. at about 50°–60° C. A slurry containing lipase and an amount of fresh water sufficient to rehydrate the lipase are introduced into the presplitter vessel along with the triglyceride to be split. The remainder of the water required for the presplitting operation is introduced separately, preferably (after or before) the addition of the lipase-fresh water. A lipase such as the lipase from *Humicola lanuginosa,* commercially available as Novo LIPOLASE™ 100T, is simultaneously introduced on a continuous basis into the reaction vessel. The flow rates of the triglyceride and of the tallow slurry are adjusted to provide from about 2% to about 5% by weight of water based on the weight of triglyceride, and to provide a residence time for the triglyceride in the reaction vessel of from about 24 to about 96 hours, depending on the temperature and on the activity of the lipase used in the process. Under these conditions, a steady state acid value in the effluent ranging from about 25 to about 100 is obtained, and usually from about 50 to about 100. The mixture in the reaction vessel is thoroughly mixed throughout the process, using any agitation or stirring means that will accomplish such thorough mixing. The fatty acids formed in the presplitter form a separate liquid phase from the sweetwater phase the principal contents of which are water, residual triglycerides, and glycerine. The sweetwater effluent from the pressure splitter is sent to a disk centrifuge to remove the residual triglycerides and then into a series of steam evaporators wherein the water is separated from the glycerine by evaporation and the evaporated water is condensed to form the glycerine evaporator condensate. The glycerine evaporator condensate is recycled to presplitter and added sequentially with respect to the fresh water-lipase slurry. The glycerine evaporator condensate can be added either before or after the addition of the fresh water-lipase slurry. If the glycerine evaporator condensate and fresh water-lipase slurry are added simultaneously to the presplitter, the lipase will be inactivated.

The triglycerides which can be used in the process according to the invention include but are not limited to tallow, lard, coconut oil, canola oil, palm oil, and mixtures thereof. The preferred lipase is a 1,3-position specific enzyme. This type of lipase cleaves the ester linkage at the 1 and 3 positions on the triglyceride, but leaves the remaining ester linkage intact. Preferred lipases include the lipase from *Humicola lanuginosa,* commercially available as Novo LIPOLASE™ 100T and the lipase derived from *Burkholderia cepacia,* ATCC 21,808, as described in U.S. Pat. No. 3,875,007, the entire contents of which are incorporated herein by reference. Other preferred lipases are those derived from *Mucor miehei, Candida cylindracea,* or *Rhizopus arrhizus.* Combinations of these lipases can also be used.

The following examples are meant to illustrate but not to limit the invention.

Example 1

DM Tallow Presplitting Using Fresh Water

A total of 44 million pounds of DM tallow (AV=7.3) was presplit to an acid value of 48.4 by feeding DM tallow (30,450 lb/hour) to a continuous presplitting reactor (2.5 MM lb working volume) equipped with a 10 hp blending agitator. LIPOLASE™ 100T was rehydrated in a portion of the city water feed and added simultaneously with the fat and city water fed to the reactor to give a water/tallow feed ratio of 2.36% and a lipase/tallow feed rate of 74.3 ppm. The presplit tallow effluent was then processed on a high pressure splitter at feed rates 15%–18% higher than can be achieved using non-presplit DM tallow. Presplitting by this method caused a carryover of some fatty acids and unreacted glycerides into the sweetwater, which is normally recovered by centrifugation for reprocessing, while at normal levels with this presplit raw material, was not efficiently recovered by the centrifuge. The centrifuged sweetwater was uncharacteristically hazy and an unusually large thick layer of fatty acids, fatty acid soaps, and glycerides accumulated in downstream processing tanks. The centrifuged sweetwater was concentrated in a quadruple effect evaporator then, upon distillation, gave an unusually large amount of residue, which corresponded to the lower amount recovered by the centrifuge, leading to an additional loss of valuable glycerine. Distillation reboilers required much more frequent clean-outs. Finally, it was discovered the fat accumulated and fouled finished produce bleaching beds. It was believed that minerals from the city water used in the earlier presplitting step caused these problems.

Example 2

Presplitting Performance Using Glycerine Evaporator Condensate Water

Figure 2:
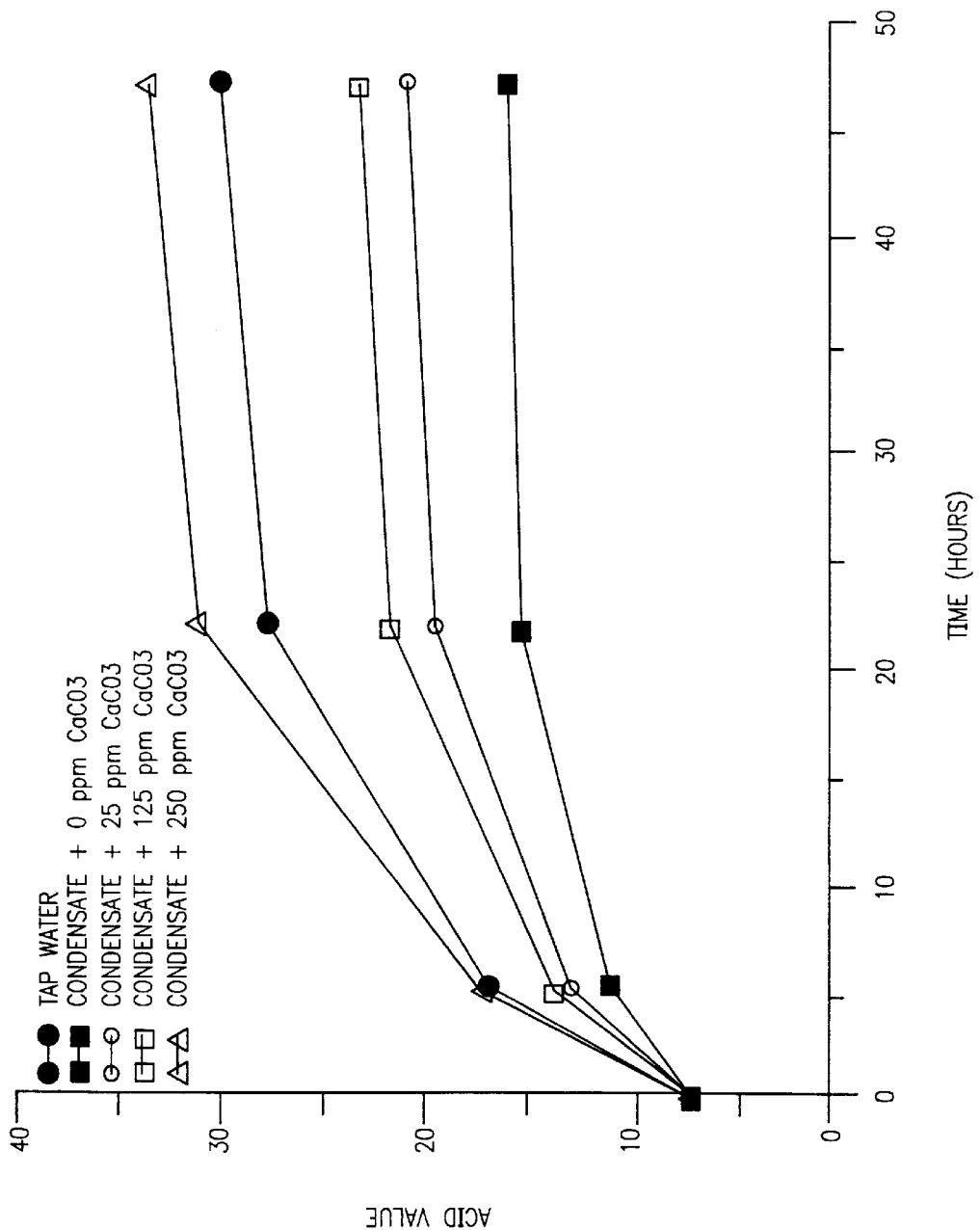
FIG. 2 is a graph of acid value of the water phase in the presplitter as a function of time. An aqueous phase from glycerine evaporator condensate which has been completely neutralized gives the greatest acid value increase indicating that the triglycerides are being split into fatty acids.

Glycerine evaporator condensate water was compared with fresh (city) water in laboratory presplitting tests. LIPO- LASE™ 100T (0.1467 g) was rehydrated in 100 ml of city water or cooled evaporator condensate water at room temperature. These stock solutions (0.3 ml) were each added to 10 g of tallow with stirring at 60° C. to observe the effect of water on presplitting performance. The results, shown in FIG. 2 (closed symbols), indicate that evaporator condensate water has a detrimental effect on presplitting performance. It was concluded that the condensate water could not be directly substituted for city water in the process of example 1.

Example 3

Neutralization of Glycerine Evaporator Condensate Water

The pH of condensate water is about 3.5–4.5 by virtue of many C1–C12 acids that tend to accumulate in the evaporator condensate during sweetwater evaporation. These may be readily neutralized by using, for example, caustic soda, calcium carbonate, lime, or slake lime. The amount of these bases required to neutralize the short chain acids is readily determined from an acid value measurement on the water. This was tested using a cooled evaporator condensate sample (AV=0.28) and adding calcium carbonate at various levels up to 250 ppm which is the amount required for complete neutralization. The partially and completely neutralized evaporator condensate was used to rehydrate the LIPOLASE™ 100T as in example 2. The results also shown in FIG. 2 (triangular symbols) demonstrate that normal presplitting performance can be achieve by completely neutralizing the short-chain acids.

Example 4

DM Tallow Presplitting Using Glycerine Evaporator Condensate Water

An alternative approach to example 1 was attempted in which substantially all the water of hydrolysis was supplied using uncooled and unneutralized evaporator condensate and a minor amount of city water was used to prepare a concentrated lipase slurry added during the presplitting reaction. Thus, a total of 29 million pounds of DM tallow (AV=8) was presplit to an average acid value of 48.4 by feeding DM tallow (37,900 lb/hr) to a continuous presplitting reactor (2.6 million pounds working volume) which was agitated with a 10 hp blending agitator. LIPOLASE™ 100T was added at an enzyme/fat feed ratio of 79.2 ppm by first making a slurry in city water (6–7 lb LIPOLASE™ 100T/4 gallons city water). The remaining major amount of hydrolysis water was added using hot untreated sweetwater evaporator condensate at a water/fat feed ratio of 2.52%.

What is claimed is:

1. A process for continuously producing carboxylic acids and glycerin from a glyceride comprising:
    (a) providing a glyceride;
    (b) providing a slurry consisting of lipase and fresh water;
    (c) providing a source of recycled water;
    (d) separately introducing (a)–(c) into a presplitter and producing a partially split glyceride, wherein the recycled water is introduced into the presplitter either before or after the introduction of (b);
    (e) mixing said partially split glyceride in a pressure splitter with water under conditions of temperature and pressure effective to complete splitting of the glyceride into carboxylic acids and an aqueous glycerin solution;
    (f) separating the water from the aqueous glycerin solution to obtain glycerin and the source of recycled water; and
    (g) diverting the source of recycled water to step (d).

2. The process of claim 1 wherein said partially split glyceride has an acid value of at least about 40.

3. The process of claim 1 wherein said temperature in said pressure splitter is in the range of about 200° to about 300° C.

4. The process of claim 1 wherein said temperature in said pressure splitter is in the range of about 240° to about 280° C.

5. The process of claim 1 wherein said pressure in said pressure splitter is in the range of about 450 to about 950 psi.

6. The process of claim 1 wherein said glyceride is selected from the group consisting of tallow, lard, coconut oil, canola oil, palm oil, and mixtures thereof.

7. The process of claim 1 wherein step (d) is conducted at a temperature less than about 70° C.

8. The process of claim 1 wherein said lipase is selected from the group consisting of a lipase derived from *Burkholderia cepacia*, ATCC 21,808, *Mucor miehei, Candida cylindracea, Rhizopus arrhizus,* and *Humicola lanuginosa.*

9. The process of claim 8 wherein said lipase is selected from a group consisting of a lipase derived from *Burkholderia cepacia,* ATCC 21,808 and *Humicola lanuginosa.*

10. The process of claim 9 wherein said lipase is the lipase derived from *Burkholderia cepacia,* ATCC 21,808.

11. The process of claim 9 wherein said lipase is the lipase derived from *Humicola lanuginosa.*

* * * * *